US 12,179,146 B2

(12) United States Patent
Doyle

(10) Patent No.: US 12,179,146 B2
(45) Date of Patent: Dec. 31, 2024

(54) APPARATUS AND SYSTEM FOR A MOLECULAR IMPRINTED AIR FILTER

(71) Applicant: Utah Valley University, Orem, UT (US)

(72) Inventor: Timothy Edwin Doyle, Orem, UT (US)

(73) Assignee: Utah Valley University, Orem, UT (US)

( * ) Notice: Subject to any disclaimer, the term of this patent is extended or adjusted under 35 U.S.C. 154(b) by 1070 days.

(21) Appl. No.: 17/021,874

(22) Filed: Sep. 15, 2020

(65) Prior Publication Data

US 2021/0387143 A1  Dec. 16, 2021

Related U.S. Application Data

(63) Continuation-in-part of application No. 16/917,469, filed on Jun. 30, 2020, which is a continuation-in-part of application No. 16/900,682, filed on Jun. 12, 2020.

(51) Int. Cl.

| | |
|---|---|
| *B01L 3/00* | (2006.01) |
| *B01D 39/16* | (2006.01) |
| *B01D 53/85* | (2006.01) |
| *B01F 23/00* | (2022.01) |
| *B01F 23/41* | (2022.01) |

(Continued)

(52) U.S. Cl.
CPC ......... *B01D 53/85* (2013.01); *B01D 39/1623* (2013.01); *G01N 33/5438* (2013.01); *G01N 33/56983* (2013.01); *B01D 2239/0414* (2013.01); *C02F 2201/4616* (2013.01); *C08G 2340/00* (2013.01); *C12Q 2565/607* (2013.01);
(Continued)

(58) Field of Classification Search
CPC ............... B01D 53/85; B01D 39/1623; B01D 2239/0414; B01D 2239/0442; B01D 2239/0471; B01D 2239/0613; B01D 2258/06; G01N 33/5438; G01N 33/56983; G01N 2333/005; G01N 2600/00; C02F 2201/4616; C08G 2340/00; C12Q 2565/607; Y02A 50/20

See application file for complete search history.

(56) References Cited

U.S. PATENT DOCUMENTS

| | | |
|---|---|---|
| 5,070,243 A | 12/1991 | Bornstein et al. |
| 8,357,275 B2 | 1/2013 | Vanaja et al. |

(Continued)

FOREIGN PATENT DOCUMENTS

WO      2008116165 A2      9/2008

OTHER PUBLICATIONS

U.S. Appl. No. 16/900,682, "Office Action Summary", USPTO, Aug. 9, 2023, pp. 1-51.

(Continued)

*Primary Examiner* — Jennifer Wecker
*Assistant Examiner* — Oyeleye Alexander Alabi
(74) *Attorney, Agent, or Firm* — Kunzler Bean & Adamson

(57) ABSTRACT

Disclosed herein is a molecular imprinted air filter for removing, detecting and/or reporting specific agents and/or molecules and comprising one or more air-permeable layers of molecular imprinted material positioned to contact molecules and/or agents in an airborne, and/or microdroplet-borne environment, a bioactive molecular imprint of a molecule that captures a specific airborne, fluid borne, and/or microdroplet-borne molecule, particle, or agent, and an electronic enhancement.

16 Claims, 10 Drawing Sheets

(51) Int. Cl.
  *B01F 101/23* (2022.01)
  *B23Q 17/24* (2006.01)
  *C08J 3/075* (2006.01)
  *C08K 3/16* (2006.01)
  *C08K 3/22* (2006.01)
  *C08K 3/32* (2006.01)
  *C12Q 1/18* (2006.01)
  *G01N 21/64* (2006.01)
  *G01N 27/411* (2006.01)
  *G01N 33/50* (2006.01)
  *G01N 33/543* (2006.01)
  *G01N 33/569* (2006.01)

(52) U.S. Cl.
  CPC ... *G01N 2333/005* (2013.01); *G01N 2600/00* (2013.01)

(56) References Cited

U.S. PATENT DOCUMENTS

| | | | |
|---|---|---|---|
| 8,366,625 | B2 | 2/2013 | Burns et al. |
| 9,562,855 | B1 | 2/2017 | Yoon et al. |
| 9,678,005 | B1 | 6/2017 | Yoon |
| 2004/0089156 | A1* | 5/2004 | Gartstein ............ B03C 3/16 96/53 |
| 2004/0250683 | A1* | 12/2004 | Soane ............ B01D 46/10 55/528 |
| 2007/0163588 | A1* | 7/2007 | Hebrank ........ A61M 16/0069 128/205.29 |
| 2012/0016252 | A1 | 1/2012 | Melker et al. |
| 2016/0317848 | A1* | 11/2016 | Zilberstein ............ B03C 3/70 |
| 2016/0361674 | A1* | 12/2016 | Swaminathan ........ B01D 39/04 |
| 2018/0144092 | A1 | 5/2018 | Flitsch et al. |
| 2019/0105458 | A1* | 4/2019 | Hammes ............ A61L 9/122 |
| 2021/0386133 | A1 | 12/2021 | Doyle |
| 2021/0386142 | A1 | 12/2021 | Doyle |
| 2023/0103369 | A1* | 4/2023 | Gluckman ........ G01N 33/56983 435/5 |

OTHER PUBLICATIONS

U.S. Appl. No. 16/917,469, "Office Action Summary", USPTO, Aug. 23, 2023, pp. 1-47.

"Panda" http://www.panda-pcb.com/html/Products/Interdigital-Electrodes.html (Year: 2019).

* cited by examiner

APPARATUS AND SYSTEM FOR A MOLECULAR IMPRINTED AIR FILTER

FIELD OF THE INVENTION

This invention relates to the field of air filtration and more particularly relates to a molecular imprinted agent-specific air filter.

BACKGROUND

Air filtration systems are widely used to remove microscopic airborne particles (i.e., aerosols) from the circulating air of enclosed areas including buildings, rooms, curtained enclosures, tents, passenger aircraft, passenger trains, monorails, cruise ships, ferries, automobiles, buses, and other vehicles. Hazmat suits with supplied air respirator hoods or helmets would also qualify as enclosed areas for individual occupants. The majority of air filtration systems use filters that employ three primary collection mechanisms: Diffusion, interception, and inertial impaction. Air filtration systems may also use microporous carbon, such as activated carbon or carbon cloth, to remove hazardous gases, organic compounds, and/or odor molecules. Microporous carbon filters are not effective, however, at trapping and/or killing bacteria or viruses.

Several standards have been used to rate the performance of air filters. In the United States ASHRAE 52.2 was the most widely used standard, whereas in Europe EN779:2012 was the principal standard. Both of these standards employed the Minimum Efficiency Reporting Value (MERV), which defined the filter efficiency as the number of particles captured by the filter. One issue with MERV is that it is strongly biased to particles larger than 3 micrometers in diameter, which only comprise approximately 0.20% of the total number of airborne particles. Additionally, the most dangerous atmospheric particles are smaller than 3 micrometers in diameter.

ASHRAE 52.2 and EN779:2012 were supplanted by ISO 16890 in 2017. ISO 16890 is a global standard that incorporates particle size as well as particle concentration, and also addresses particles smaller than 3 micrometers. To address particle size, ISO 16890 uses a classification system widely used for characterizing particulate air pollution consisting of solid particles and liquid microdroplets. ISO 16890 defines four classifications of particulates (where PM denotes particulate matter):

PM1 (particles with diameters less than or equal to 1 micrometer),
PM2.5 (particles with diameters less than or equal to 2.5 micrometers),
PM10 (particles with diameters less than or equal to 10 micrometers),
PM coarse (particles with diameters greater than 10 micrometers).

With ISO 16890, the efficiencies of air filters are rated with respect to each of the four particle size classifications, providing four efficiency values with which to rate the filter. The ISO 16890 standard is also in accord with the particle-size method that the World Health Organization uses to determine air quality.

Current air filters, therefore, primarily use mechanical interactions, such as inertial impact, to capture airborne particles. The filtration material on an air filter is typically an electrostatic non-woven polypropylene fiber. Fiber density (number of fibers per volume) in the filter is also tailored to trap particles of a specific diameter range, and to optimize the number of particles collected. Additional technologies may infuse filtration surfaces with various metal ions such as copper to provide some degree of antimicrobial function. However, current filtration surface coating technologies do not incorporate all desirable aspects, such as agent specific anti-microbial action or detection and reporting of captured agents. Many filters, such as HEPA filters, are sometimes designated as "antimicrobial" because they are efficient at trapping particle sizes that correspond to those of allergens such as pollen and mold spores, microorganisms such as bacteria, or microdroplets that may transport viruses. The filtration material on an air filter is typically an electrostatic non-woven polypropylene fiber. Additional technologies may infuse filtration surfaces with various metal ions such as copper to provide some degree of anti-microbial function. However, current filtration surface coating technologies do not incorporate all desirable aspects, such as agent specific anti-microbial action. Additional technologies may infuse the fiber matrix of the filter with broad-spectrum antimicrobial compounds to provide some degree of antimicrobial function. Other antimicrobial air filtrations systems may include photocatalytic systems and ultraviolet (UV) light systems, although UV light systems would only be effective at sterilizing filters once they have captured the microbes since several minutes of UV light exposure are usually required to kill bacteria and viruses.

Current air filter technologies, therefore, have limited antimicrobial capabilities and do not incorporate all desirable aspects, such as agent specific capture, antimicrobial action, and reporting. Such an agent specific antimicrobial action is difficult to achieve with nonselective mechanical interactions, particle segregation by size, broad-spectrum antimicrobial agents, or photocatalytic systems. Thus, a need exists for an apparatus incorporating the action of a specific molecule and/or a mixture of molecules targeted to specific agents including specific pathogens. Targeting specific pathogens in air filters would improve the efficiency of air filters since a much larger surface area in the filter could be provided for capturing and deactivating the targeted pathogen. Beneficially, the capacity of such an agent specific filter could be sized for a building, room, tent, patient enclosure, individual enclosure or vehicle.

SUMMARY

From the foregoing discussion, it should be apparent that a need exists for an air filtration system for occupied enclosures that would protect against specific infectious agents. It should further be apparent that a need exists for an air filtration system with antimicrobial properties that arise from specific biochemical mechanisms. Beneficially, such an apparatus could be self-cleaning and could detect in real time and optionally report the presence and/or concentrations of specific infectious agents.

The present invention has been developed in response to the present state of the art, and in particular, in response to the problems and needs in the art that have not yet been fully solved by currently available air filtration systems. Accordingly, the present invention has been developed to provide a molecular imprinted air filtration system that overcomes many or all of the above-discussed shortcomings in the art.

Provided herein is a molecular imprinted air filter apparatus for removing, detecting and/or reporting specific agents and/or molecules, the apparatus comprising an air filtration element comprising one or more air-permeable layers of molecular imprinted or outprinted fabric, woven material, non-woven material and/or a porous material positioned to contact molecules and/or agents in an airborne, fluid borne and/or microdroplet-borne environment, a bioactive molecular imprint wherein an imprinted cavity is of at least one of a bioactive molecule that captures a specific airborne, fluid borne, and/or microdroplet-borne molecule, particle, or agent, and of a protein with a binding site that captures a specific airborne, fluid borne, and/or microdroplet-borne molecule, particle, or agent, a power access, and an electronic enhancement.

In certain embodiments the air filtering component comprises an air-permeable material comprising at least one of paper, polymer foam, woven fabric, knitted fabric, nonwoven fabric, melt-blown fabric, ion-infused fabric, a nonfabric material and a hydrophilic material to capture airborne droplets to enable the interaction of the molecular imprint cavities with airborne hazardous substances and/or infectious pathogens in an aqueous environment.

The apparatus may further comprise an air intake avenue and an air output avenue and/or a fluid supply and associated fluid automizer. In some embodiments the electronic enhancement comprises an interdigital electrode, a conducting electrode, a semiconductor, a nanoparticle quantum dot, a nano-island, a quantum wire, other nanostructured component, a sensor wire, a piezoelectric element, an acoustic waveguide, an optical waveguide, an optical fiber, an ultrasonic transducer, and/or a laser. The conductive electrode may function as an interdigital electrode for enhancing, modulating, and/or reading the binding state of the imprinted cavities.

In various embodiments the interdigital electrode comprises comb-shaped interlocking arrays of straight parallel electrodes, a fan-shaped array of radially oriented electrodes, an array of concentrically oriented circular electrodes, and/or arrays consisting of electrodes arranged in more complex geometries such as elliptical, parabolic, hyperbolic, and straight-line angles.

The electronic enhancement may generate a static and time-varying electrical field, produce an electron wave function configuration that dynamically reconfigures the electron charge distribution within the molecular imprint, enable fine tuning of the imprinted cavity to enhance its response to a range of molecules, generate ultrasonic and/or electromagnetic waves providing energy to free molecules from the imprinted cavity, mechanically agitate a biomolecule to induce its interaction with or release from the molecular imprint cavity and/or re-activate the specific molecule capture function of the imprinted cavity.

The filtration component and/or the molecular imprint cavity sometimes comprises a biosensor for a specific health condition, a specific type of pathogen, a specific type of pollutant, a specific type of allergen, and/or a specific environment or condition and/or is customized to a specific user or set of users.

In certain embodiments the biosensor comprises a molecular imprinted polymer surface and devices employing surface plasmon resonance (SPR), surface-enhanced Raman spectroscopy (SERS), stimulated Raman spectroscopy (SRS), Mie scattering spectroscopy, fluorescence quenching of semiconductor quantum dots, photoluminescence, UV-visible spectroscopy, electrochemical sensors (conductivity, capacitance, impedance, potentiometry, and voltammetry measurements), piezoelectric sensors (quartz crystal microbalance, acoustic waveguide, surface acoustic wave (SAW), pulse-echo ultrasound, through-transmission ultrasound, and phased-array ultrasound), and/or biomimetic microchips with micropatterned imprinted polymers. The electronic enhancement may read the binding state of the molecular imprinted cavities to detect hazardous airborne and/or microdroplet-borne agents, report the presence of a specific agent, and/or trigger re-tuning the imprinted cavities in response to a completed reaction and/or a changing molecular environment.

In various embodiments the molecular imprinted air filter comprises one or a plurality of types of molecular imprint cavities wherein the one or more layers of the filtering component catalyze a biochemical reaction with an airborne, fluid borne, and/or microdroplet-borne agent to attenuate, neutralize, and/or detect the agent. In some embodiments each layer of the filtering component catalyzes a particular step of a biochemical reaction with an airborne and/or microdroplet-borne agent to attenuate, neutralize, and/or detect the agent. Layer (n) may catalyze a particular biochemical reaction (p) in a multistep reaction with an airborne and/or microdroplet-borne agent. Layer (n+1) may catalyze a successive biochemical reaction (p+1) in a multistep reaction with an airborne and/or microdroplet-borne agent. The plurality of molecular imprint cavity types may catalyze a multistep biochemical reaction to attenuate, neutralize, or detect an airborne and/or microdroplet-borne agent. The plurality of molecular imprint cavity types sometimes simultaneously catalyzes one or more biochemical reactions to attenuate, neutralize, detect, and/or report one or more hazardous airborne and/or microdroplet-borne agents.

Further provided herein is a molecular imprinted air filtration system for removing, detecting and/or reporting specific agents and/or molecules and comprising; an air filtering component comprising one or more air-permeable layers of molecular imprinted fabric, woven material, nonwoven material and/or a porous material positioned to contact molecules and/or agents in an airborne, and/or microdroplet-borne environment, a bioactive molecular imprint wherein an imprinted cavity is of a bioactive molecule that captures a specific airborne, fluid borne, and/or microdroplet-borne molecule, particle, or agent, and of a protein with a binding site that captures a specific airborne, fluid borne, and/or microdroplet-borne molecule, particle, or agent. The molecular imprinted air filtration system herein further comprises a power access, an electronic enhancement, a sensor, a sensor controller, a reporting module, a communications module, a receiving module, and a repository. The sensor controller may comprise a photodetector, an ultrasound transducer, a spectrometer to analyze optical signals with molecular spectroscopy, a multiplexer for a plurality of sensor channels, an amplifier, a rectifier for radio-frequency signals, an electronic filter and/or discriminator to separate signals from noise, and a trigger signal generator.

In certain embodiments the molecular imprinted air filtration system herein comprises one or more of a repository, a dispersal module, and an alarm in communication with a trigger selected from the group consisting of the sensor, the sensor controller, the reporting module and the communications module. The communications module may communicate with the receiving module via an alarm, a cloud system, an internet, and/or a database.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Introduction

Molecular imprinting is an advancing technique in the medical device field because of its ability to mimic biologically active binding sites. Molecular imprinting uses artificial binding sites of proteins, sugars, and other biological compounds in order to capture molecules. Numerous two-dimensional and three-dimensional techniques are known in the art for imprinting of surface proteins. Techniques using silica have shown successful specificity for imprinting complex shapes such as hemoglobin. Biomedical applications have utilized molecular imprinting for ex vivo diagnostic methods such as immunoassays (antibody detection), analytical separations, and biosensors for detecting changes in blood sugar. Molecular imprinting is also used in the development of other biosensors and for diagnostic detection of viruses by interacting with antibodies.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided to convey a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1:
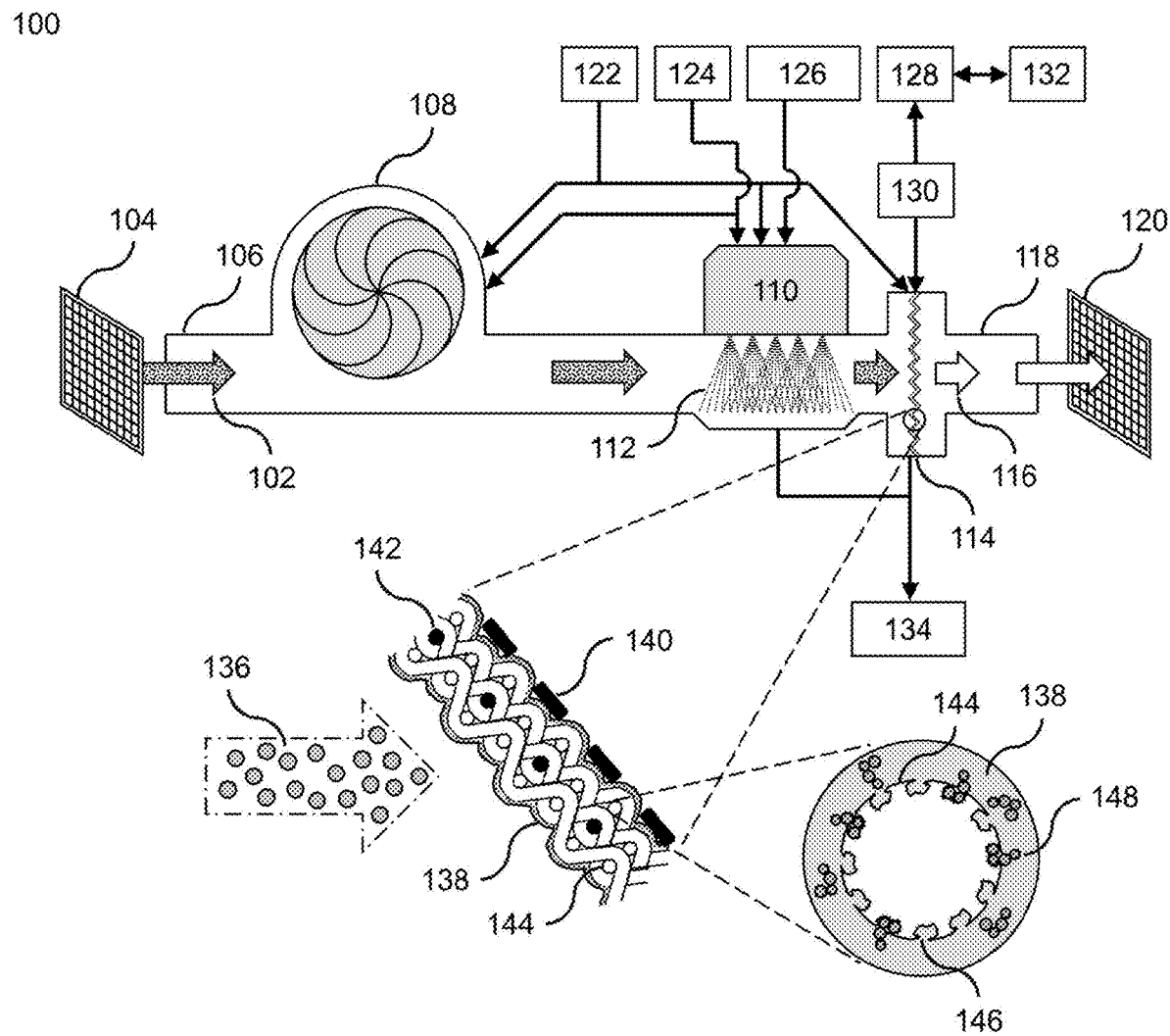
FIG. 1 is a schematic line and surface drawing depicting an embodiment of a molecular imprinted air filter in accord with the present invention.

FIG. 1 depicts an embodiment of an air filtration apparatus 100 comprising an air intake grill 104, an intake duct 106, a fan or other air flow generator 108, a mist generator or atomizer 110, water microdroplets 112, a molecular imprinted filter 114, an outflow duct 118, an outflow grill 120, a power supply 122, a controller 124 for the fan 108 and mist generator 110, a water supply 126 for the mist generator 110, a sensor 130, a sensor controller 128, a reporting module 132, a drainage reservoir 134, digital sensors 140, optical waveguides and/or acoustic waveguide sensors 142, fibers 144, and molecular imprints 146.

In certain embodiments the air filtration apparatus 100 operates as follows. Unfiltered air 102, from either outside air or the interior air of the enclosure, is drawn through the intake grill 104 and intake duct 106 by air flow generated by the fan 108. Water microdroplets 112 are then sprayed into the unfiltered air 102 by the mist generator 110. An unfiltered air/microdroplet mixture 136 then flows through the molecular imprinted filter 114. The microdroplets 112 coat the fibers 144 and the molecular imprints 146 with a thin film of water 138, which (1) significantly increases the efficiency of particle capture by the molecular imprints 146 and (2) provides an aqueous environment for the molecular imprints 146 to interact with target molecules 148 on the surface of the fibers 144. Sensors 130, 140 embedded in the molecular imprinted filter 114 are actuated and read by the sensor controller 128. In various embodiments the sensor controller 128 comprises one or more of a data processor, a data recorder, and a data display. Filtered air 116 then flows through the outflow duct 118 and outflow grill 120, exiting the molecular imprinted air filter 100 and entering the enclosed area. In certain embodiments the sensor controller 128 notifies the reporting module 132 of specific molecules detected and the reporting module 132 generates an alarm or warning. The alarm or warning may comprise an auditory alert or a visual display.

The air filtration apparatus 100 may be fabricated in a variety of different modules and with different molecular imprints 146 on the molecular imprinted filter 114. A model could then be available for capturing various types of pathogens including bacteria and viruses such as the COVID-19 virus. In certain embodiments pathogens trapped on the molecular imprints 144 of the molecular imprinted filter 114 may also be inactivated or killed. Mechanisms may include, without limitation, chemical, biological, electrical, sonic, and UV light, in applications as described below.

Figure 2:
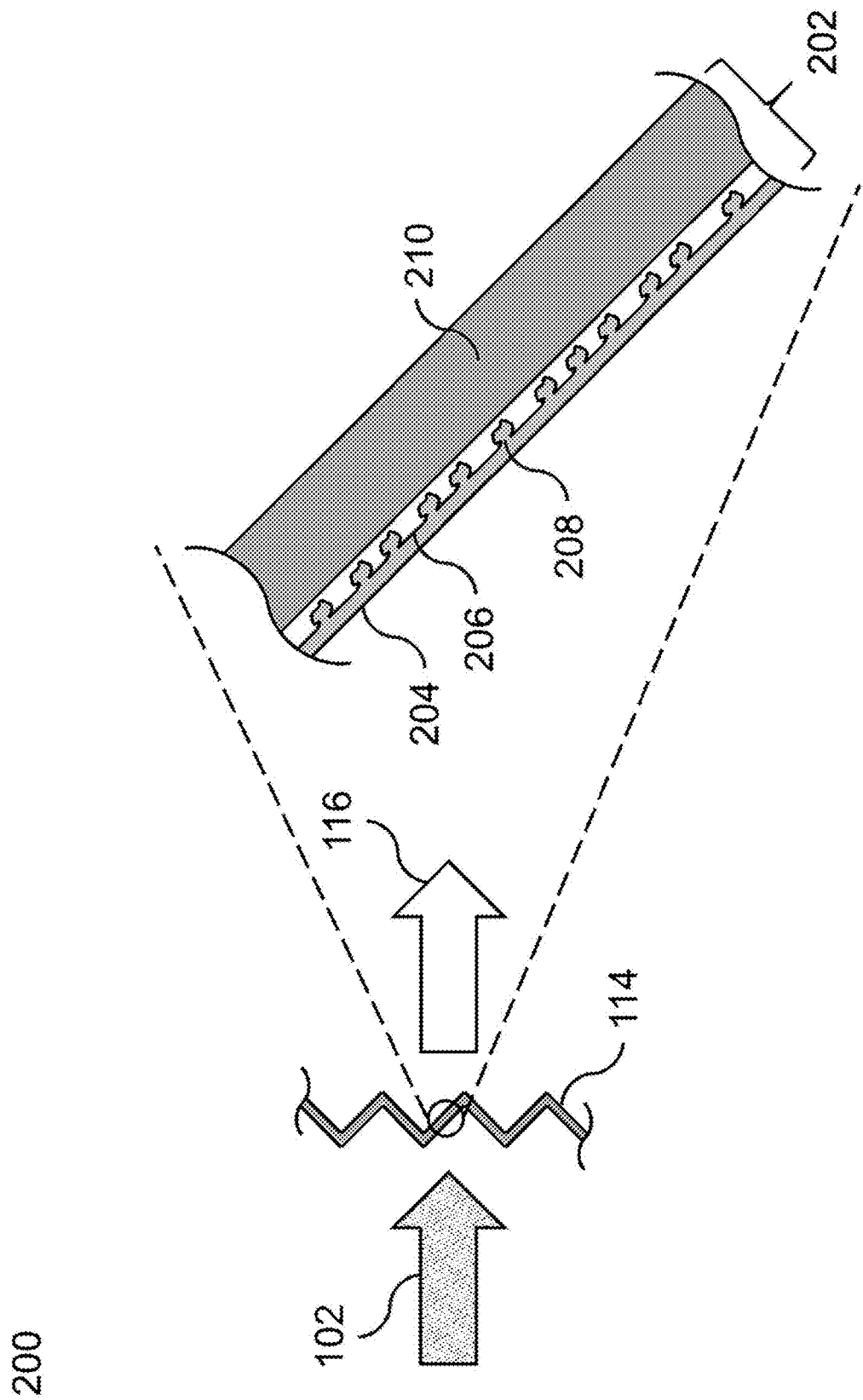
FIG. 2 is a schematic line and surface drawing depicting an embodiment of a single layer molecular imprinted filtering element in accord with the present invention.

FIG. 2 depicts an expanded view of an embodiment of a single-layered molecular imprinted filter 200 comprising a molecular imprinted filter 114 with a single layer filtration element 202, a thin polymer film 206, and molecular imprints 208 on surface of the polymer film 206, and a non-imprinted filter support 210. Unfiltered air 102 passes through the single-layer filtration element 202 molecular imprinted filter 114 and filtered air 116 emerges.

In some embodiments the single-layer filtration element 202 is coated with the thin polymer film 206. The single-layer filtration element 202 may comprise molecular imprinted fibers 144 or other porous material. The thin polymer film 206 sometimes comprises a porous membrane or a mesh with molecular imprints 208 that in various embodiments may capture, sense, destroy, and/or release bacteria, viruses, medications, and various airborne particles. The molecular imprints 208 may interact with various molecules in the presence of a thin film of water 204.

Molecular imprints 208 may be created on a thin polymer film 206 by mixing monomers of polymer with the molecule (known as the template) to be imprinted. First, the monomers cluster and conform around the template. Second, the monomers polymerize with the template in place. Third, the template is removed from the polymer, thus leaving a mold or imprint 208 of the molecule in a polymer matrix. The monomers may be polymerized into nanoparticles or thin films. To create the molecular air filtration apparatus 100 described herein, the monomers may be polymerized as a thin film 206 on the porous surface of the molecular imprinted filter 114, on the surfaces of fibers 144 comprising a fabric or woven filtering component and/or on the surface of a single-layer molecular imprinted filter 202 or on the surfaces of a multilayered molecular imprinted filter 300. The monomers are sometimes polymerized directly as fibers 144 and incorporated into a fabric or woven filtering component. The non-imprinted filter support 210 may comprise woven fabric, non-woven fabric, a random fiber sheet, a porous polymer or other material.

Various methods for the fabrication of molecular imprinted polymers as thin films on a solid substrate are known in the art, and include spin coating, polymer brushes, dip coating using a silicon substrate, self-assembling monolayers, drop coating, spray coating, grafting, electropolymerization, and sol-gel processes. Micropatterned thin films of molecular imprinted polymers can also be manufactured using various lithography methods such as UV-mask lithography, soft lithography, micro-stereo lithography, and nanoimprint lithography.

Figure 3:
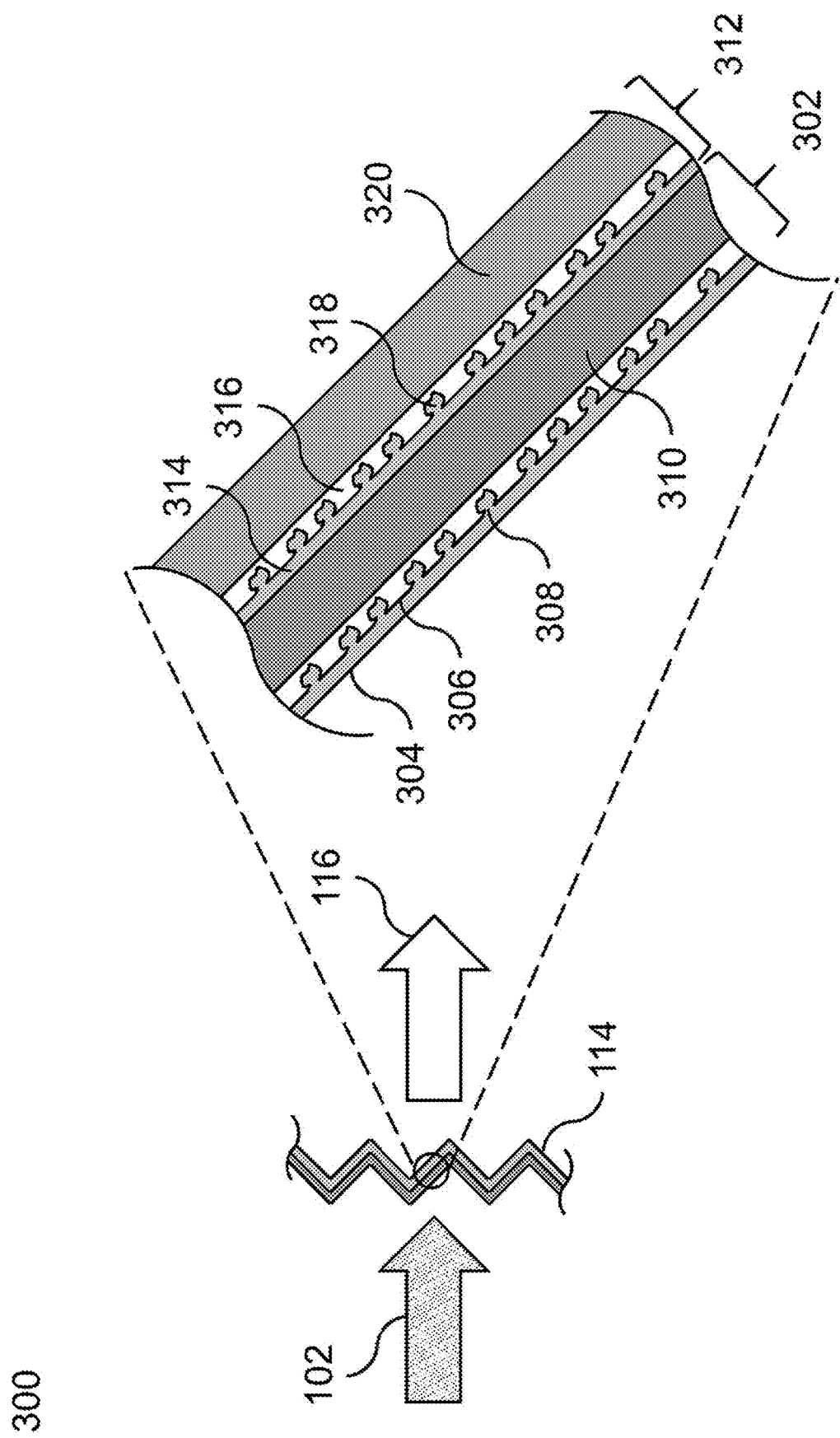
FIG. 3 is a schematic line and surface drawing depicting an expanded section view of an embodiment of a multiple layer molecular imprinted filtering element in accord with the present invention.

FIG. 3 depicts an embodiment of a multilayered molecular imprinted air filter 300 comprising a molecular imprinted filter 114, a first filtration element 302, a thin polymer film 306, type-1 molecular imprints 308, a non-imprinted filter support 310, an additional filtration element 312, a thin polymer film 316, type-1+n molecular imprints 318, and a non-imprinted filter support 320. In various embodiments of the invention, two or more layers of a molecular imprinted fabric or other material are used to generate a multi-step process to attenuate, neutralize, and/or detect toxic, hazardous, or infectious agents in the air. Two or more layers of a molecular imprinted fabric or other material may be used to detect toxic, hazardous, or infectious airborne agents in one layer, and to attenuate and/or neutralize these agents in the other layer.

The strategically placed imprints 308 and 318, as shown on the multilayered molecular imprinted filter 300 may be those of an antigen or binding site for a bacteria or virus such as COVID-19. Imprinting of an antigen or binding site may be accomplished through template imprinting techniques. Antigen or binding site molecules are obtained as a template by absorption onto a silicate mineral along with a buffer. The sample is heated and left to cool. Afterwards the sample is rinsed with deionized water to remove the buffer. The remaining sample may be coated with a disaccharide. A plasma deposition (hexafluoropropylene) may be deposited onto the sample and placed in a plasma reactor to remove the template protein. Finally, a solvent may wash away any remains of the template protein.

In certain embodiments the thin polymer film 306, 316 covers a majority of the area of the first filtration element 302 and/or the additional filtration element 312 for biochemically interacting with airborne particles, gasses, and/or molecules A pattern of molecular imprints 308, 318 of different molecular species on a polymer film 306, 316 may be used as described above. Molecular imprints 308, 318 may function as "phantom" or "virtual" molecules or binding sites to capture and immobilize pathogen molecules, to sense and report them, to kill or inactive them, and to release them during cleaning. Molecular imprints 308, 318 may interact with molecules in the presence of a thin film of water 304, 314.

Figure 4A:
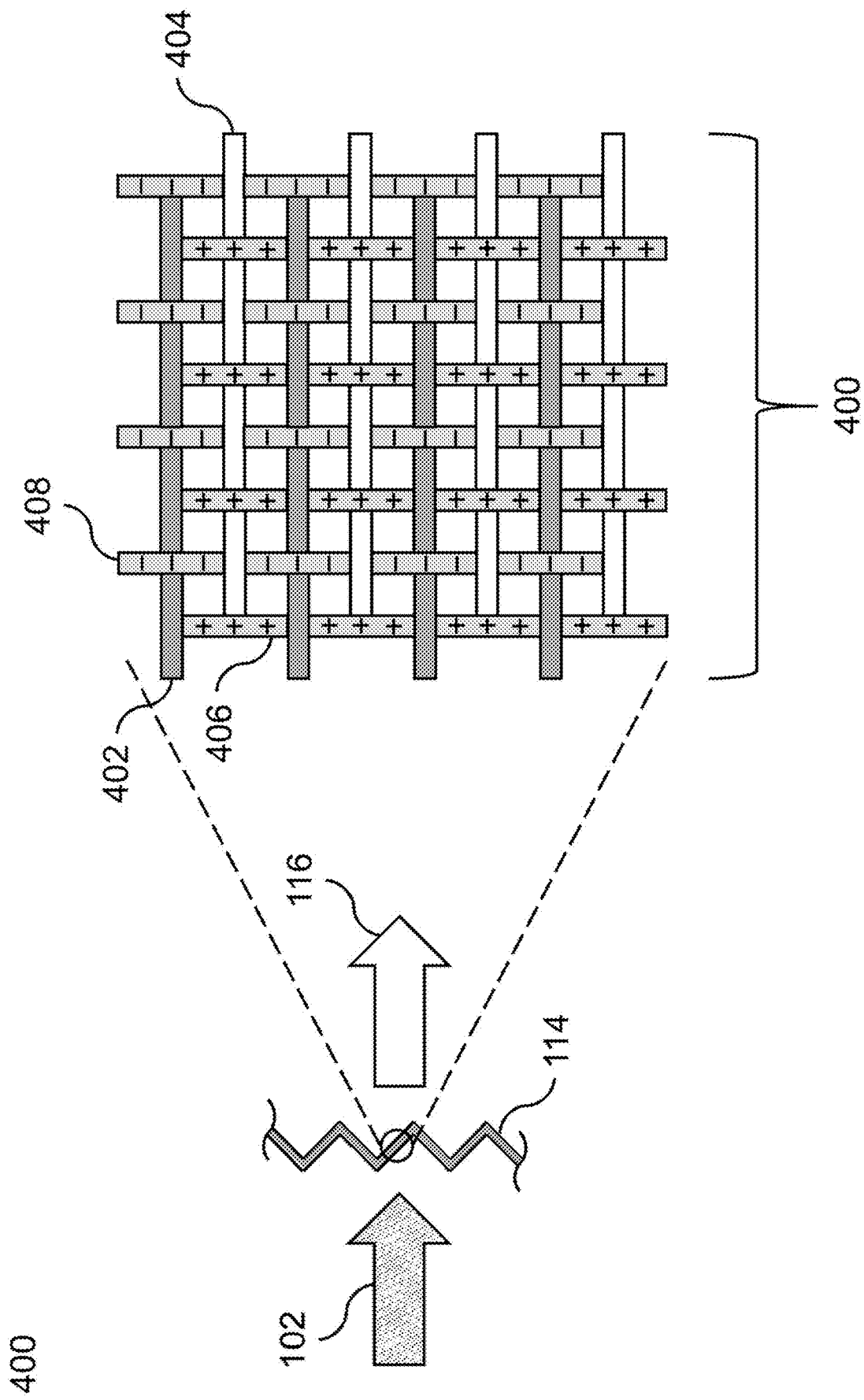
FIG. 4A is a schematic line drawing depicting an expanded section view of an embodiment of an electronically enhanced woven molecular imprinted filtering element in accord with the present invention.

FIG. 4A depicts an expanded view of an embodiment of a woven filtration element 400 of a molecular imprinted filter 114, the woven filtration element 400 comprising a molecular imprinted fiber with type-1 molecular imprints 402, a molecular imprinted fiber with type-1+n molecular imprints 404, a positive electrode (anode) 406, and a negative electrode (cathode) 408.

Figure 4B:
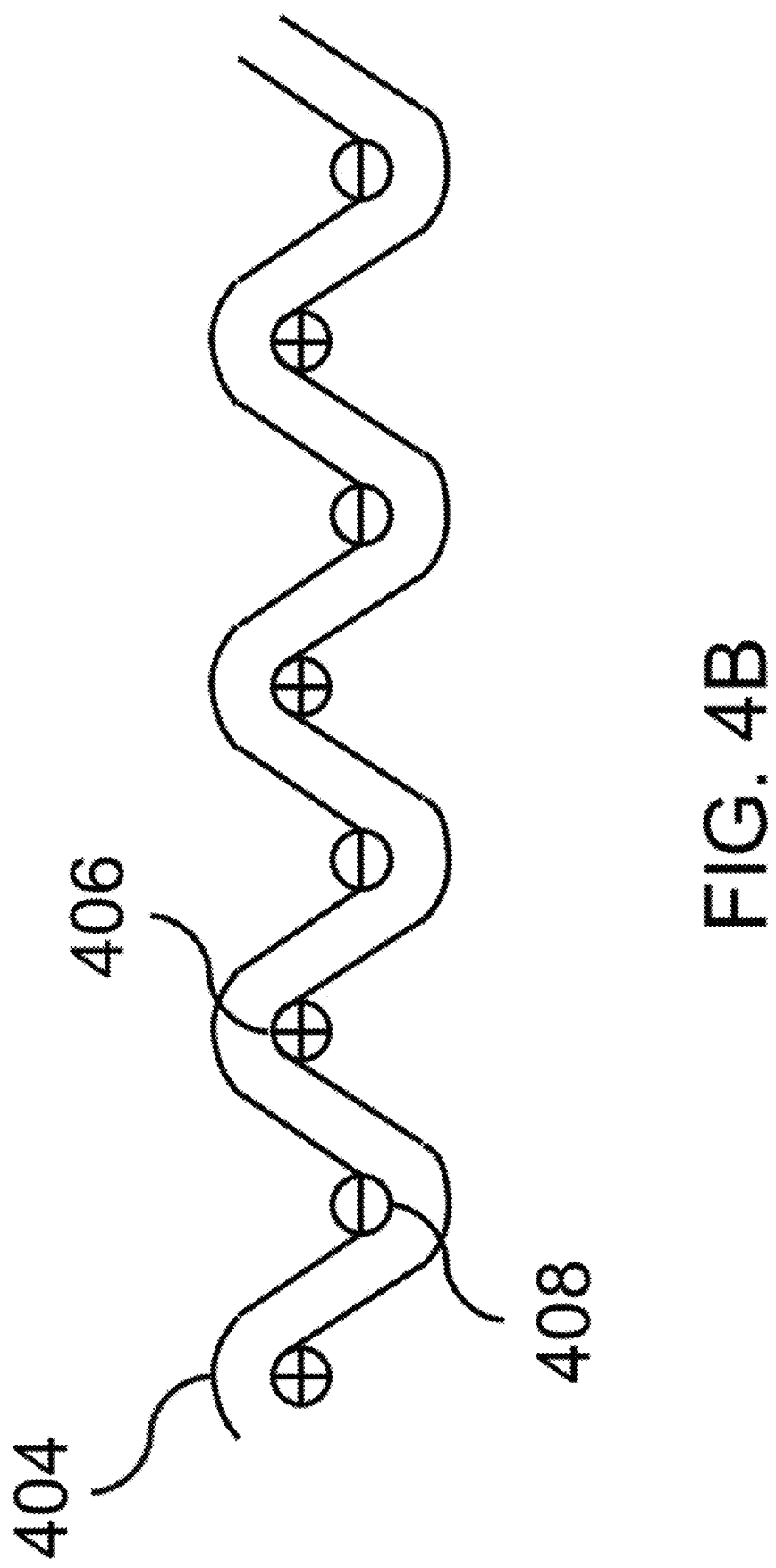
FIG. 4B is a schematic line drawing depicting an expanded side section view of an embodiment of a molecular imprinted fiber interwoven with electrodes in accord with the present invention.

FIG. 4B depicts an expanded cross section view of an embodiment of a type-n+1 fiber 404 woven between positive electrodes 406, and negative electrodes 408.

Figure 4C:
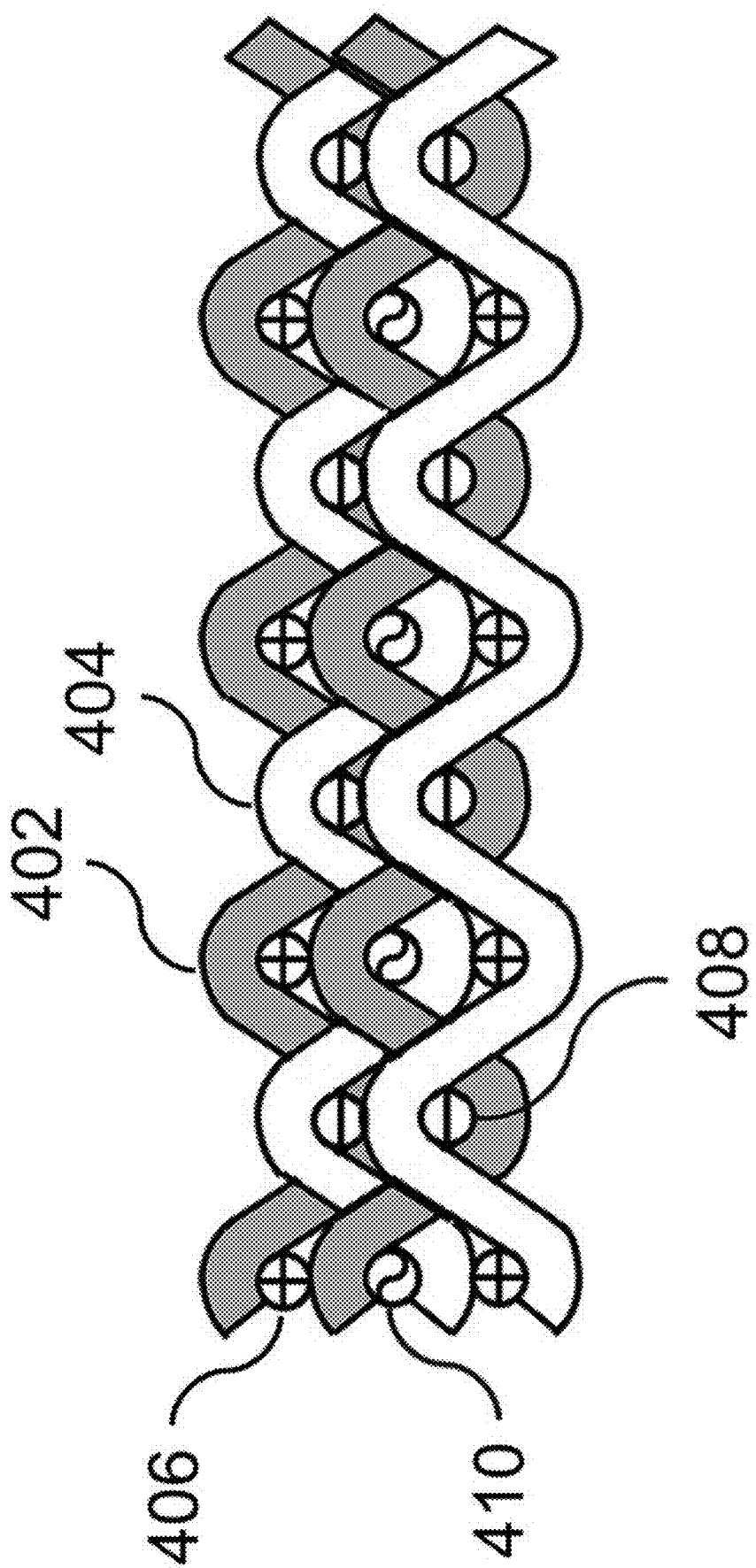
FIG. 4C is a schematic line drawing depicting an expanded side section view of an embodiment of a molecular imprinted fiber interwoven with electrodes and wave guides in accord with the present invention.
Figure 5A:
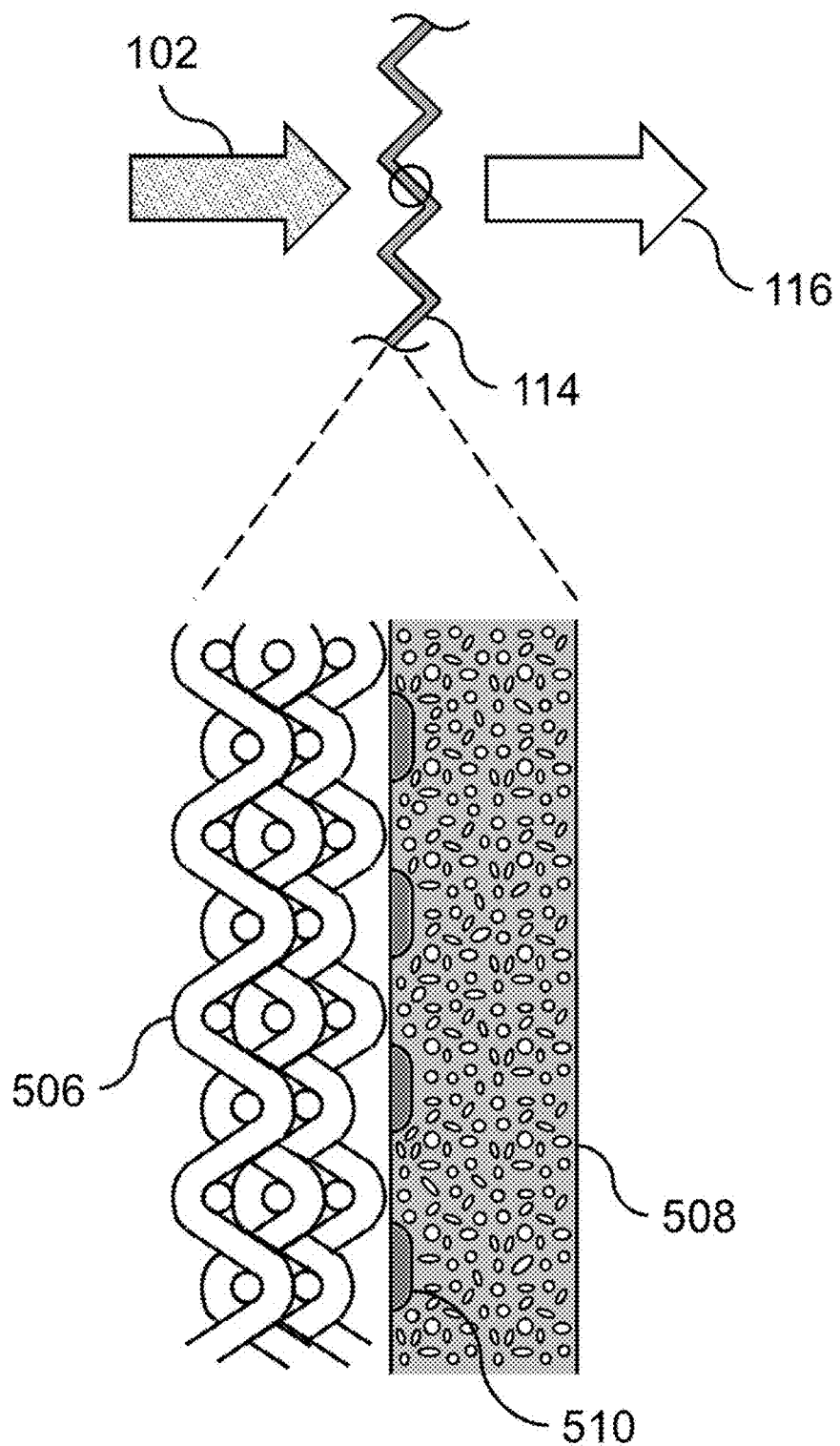
FIG. 5A is a schematic line drawing depicting an expanded side section view of an embodiment of a molecular imprinted filter with interdigital electrodes in accord with the present invention.
Figure 5B:
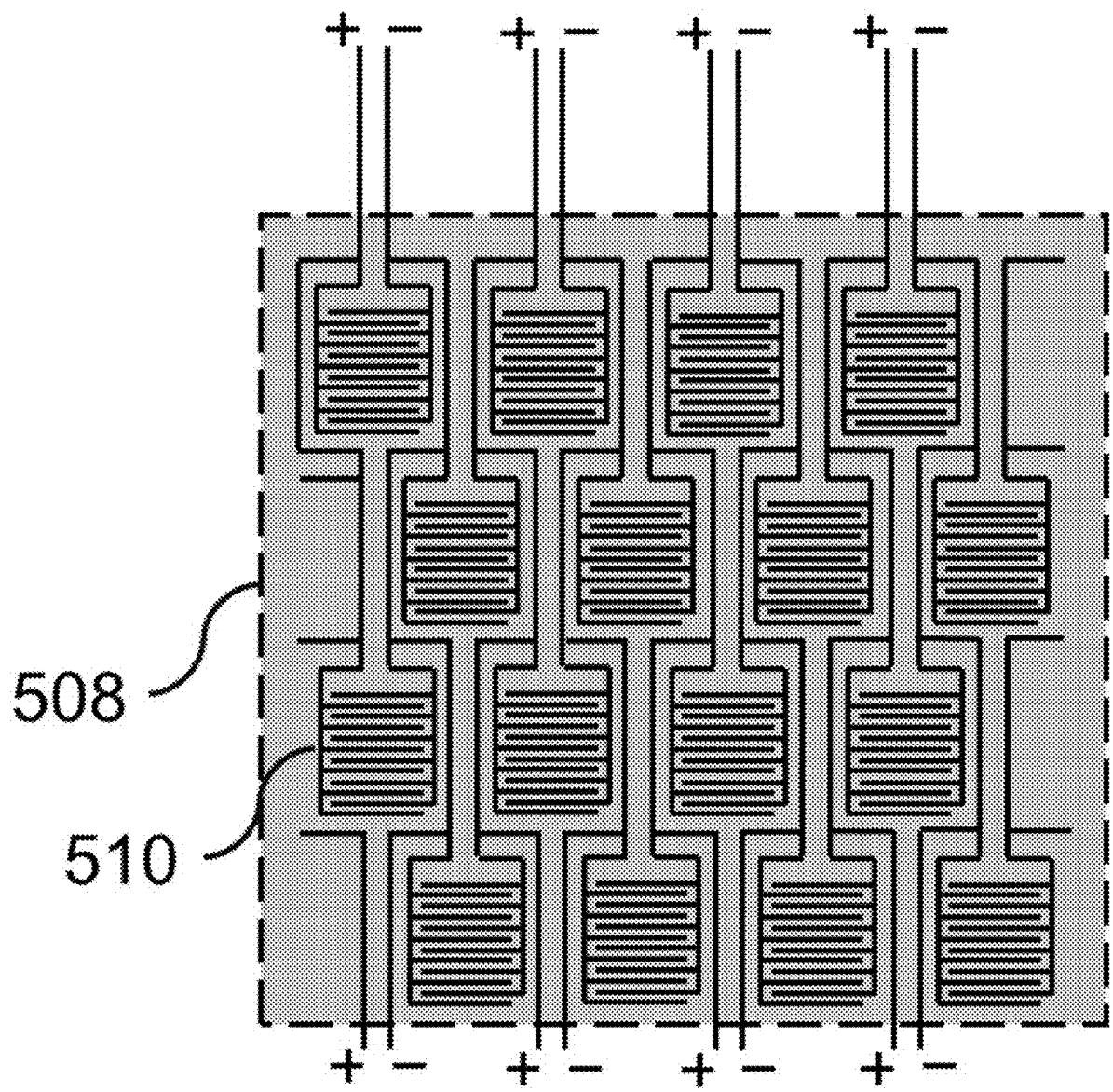
FIG. 5B is a schematic line and surface drawing depicting an expanded top section view of an embodiment of a molecular imprinted filter with interdigital electrodes in accord with the present invention.
Figure 6:
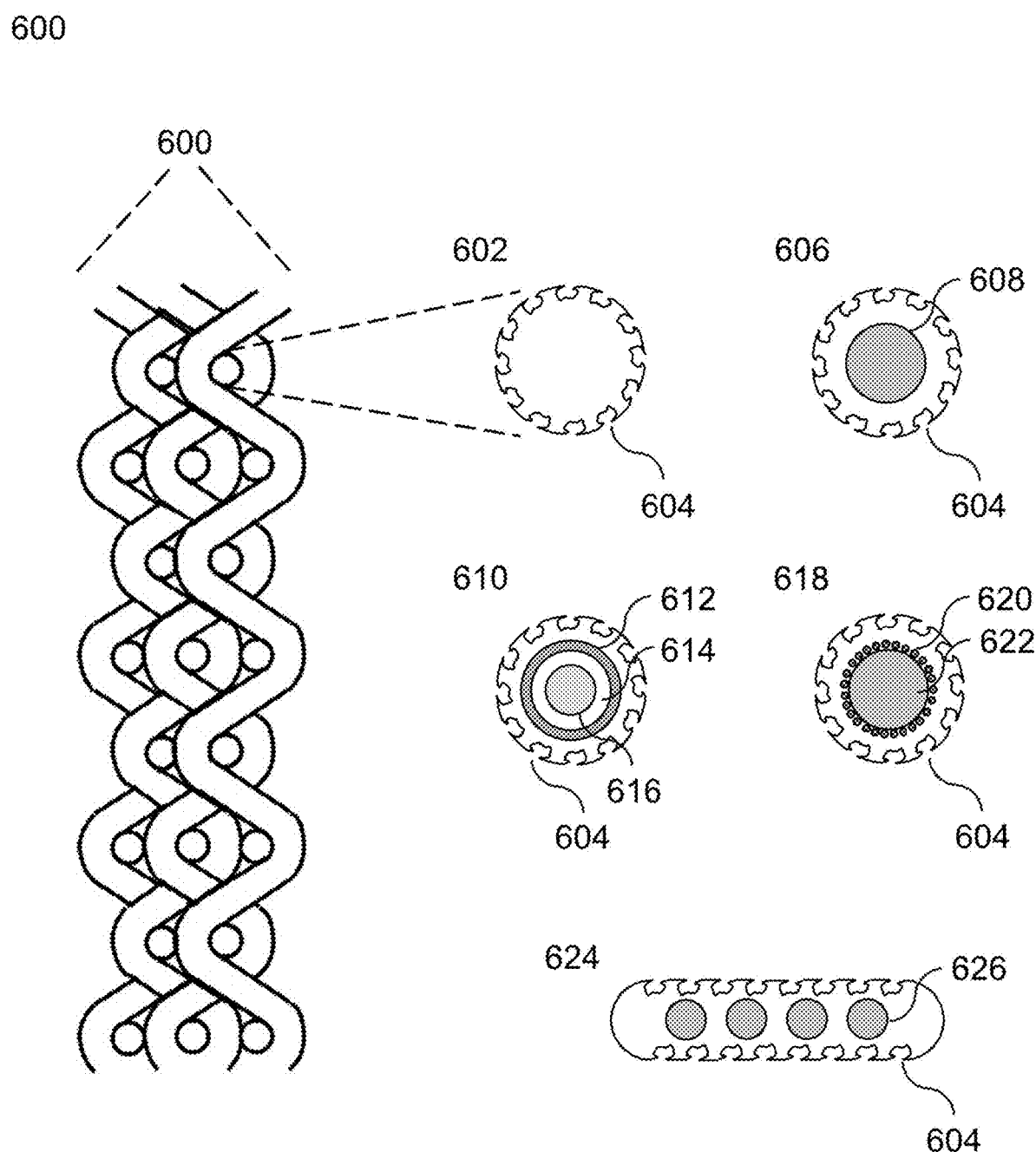
FIG. 6 is a schematic line and surface drawing depicting an expanded side section view of an embodiment of configurations of electronic enhancements in a molecular imprinted filter in accord with to the present invention.

FIG. 4C depicts an expanded cross section view of an embodiment of an optically and/or ultrasonic enhanced woven filtration element 400 comprising a molecular imprinted fiber with type-1 molecular imprints 402, a molecular imprinted fiber with type-1+n molecular imprints 404, a positive electrode (anode) 406, a negative electrode (cathode) 408, and a fiber waveguide sensor 410. In some embodiments the electrodes 406, 408 comprise metal or conductive polymer fiber. The fiber waveguide sensor 410 may be acoustical and/or optical.

Ultrasonic waves may be generated in the air filter 100, in the molecular imprinted filters 114, 200, 300, 400 or an external device and transmitted to the molecular imprinted filters 114, 200, 300, 400, to thin polymer film 206 and 306, and to molecular imprints 146, 208, 308, 318, and fibers with molecular imprints 402, 404 via waveguide principles. The acoustic waveguide 410 may comprise metal incorporated into the molecular imprinted air filter 114, 200, 300, 400. These may function according to waveguide principles such as those used to propagate light along an optical fiber and may create a vibration, mechanical agitation, or charge redistribution in the molecular imprints 146, 208, 308, 318. In this manner the molecular imprinted air filter 100 may be safely cleaned between uses and pre-loaded molecular imprints 146, 208, 308, 318 may be emptied of air treatment compounds, dispersible medication and/or other cargo. The fiber waveguide sensor 410 is coated with a thin molecular imprinted polymer film. Evanescent optical waves or acoustic waves from the fiber waveguide interact with the molecules, microorganisms, and other airborne microparticles captured by the imprints, and detectably modulate the optical or acoustic waves propagating through the waveguide. Optical and/or acoustic waveguides 410 may function as sensor components in conjunction with the molecular imprints 146, 208, 308, 318. Optical and/or acoustic waveguides 410 in a fabric, woven, or non-woven material may function to attenuate or neutralize a hazardous airborne agent. For example, ultraviolet (UV) light transmitted by optical waveguides 410 may attenuate or neutralize a virus captured by molecular imprints 146, 208, 308, 318 on the optical waveguides 410 and/or other fiber components in the fabric, woven or non-woven matrix.

FIG. 5A depicts an embodiment of an expanded cross section side view of a double layer electronically enhanced molecular imprinted filtration element 500, comprising a woven filtration layer with molecular imprinted fibers 506, a thin polymer support layer 508, and interdigital electrodes 510. The thin polymer support layer 508 may comprise a porous membrane, mesh, or other appropriate configuration.

FIG. 5B depicts an embodiment of an expanded cross section top view of a double layer electronically enhanced molecular imprinted filtration element 500 comprising a thin polymer support layer 508 and interdigital electrodes 510. In various embodiments the interdigital electrodes 510 are embedded in the thin polymer support layer 508 and/or positioned on the surface of the molecular imprinted fibers 402, 404, 506 as biosensors. In some embodiments the thin polymer support layer 508 comprises polyurethane foam.

In certain embodiments conductive wires function as interdigital electrodes 510 that enhance, modulate and/or read the binding state of molecular imprints 146, 208, 308, 318.

Biosensing molecular imprinted polymer surface technologies include surface plasmon resonance (SPR) techniques, surface-enhanced Raman spectroscopy (SERS), stimulated Raman spectroscopy (SRS), Mie scattering spectroscopy, fluorescence quenching of semiconductor quantum dots, photoluminescence, UV-visible spectroscopy, attenuated total reflection (ATR) spectroscopy, electrochemical sensors (conductivity, capacitance, impedance, potentiometry, and voltammetry measurements), piezoelectric sensors (quartz crystal microbalance, acoustic waveguide, surface acoustic wave (SAW), pulse-echo ultrasound, through-transmission ultrasound, and phased-array ultrasound), and biomimetic microchips with micropatterned imprinted polymers. The molecular imprinted biofunctional devices provided herein may combine biosensors with bioactive molecular imprints and apply them to an air filter.

In some embodiments the electronically enhanced molecular imprinted filtration element 500 is tuned to sense specific pathogens, particles, allergens, and/or volatile organic compounds (VOCs) in the environmental air. The electronically enhanced molecular imprinted filtration 500 may be tuned to a specific environment or condition and/or be customized to a specific user or set of users. Thus, the molecular imprinted air filter 100 may sense and report the status of the environmental air in real time, may trigger an alert and/or may trigger release of an appropriate dispersible material. By way of non-limiting example, the environmental air may be that of a venue, a vehicle, a home, a hospital, a room, a tent, a patient enclosure, or other location.

FIG. 6 depicts an expanded section view of an embodiment of electronically enhanced molecular imprinted fibers 500 comprising any or all of a molecular imprinted monofilament polymer fiber 602 with molecular imprints 604, a coaxial fiber 606 with a conductive core 608 and a polymer sheath with molecular imprints 604, a piezoelectric molecular imprinted fiber 610 with a conductive shield 612, a piezoelectric polymer 614, a conductive core 616 and molecular imprints 604, a coaxial fiber with nanoparticles 618 having nanoparticle quantum dots 620, a conductive core 622 and molecular imprints 604, and a non-spherical molecular imprinted fiber with a plurality of cores 624 having conductive cores 626 and molecular imprints 604. As depicted, fiber 624 is configured as a ribbon, increasing the surface area of the fiber and thereby the density of molecular imprints 604. Conductive cores 608, 616, 622, and 626 may comprise without limitation metal wire or a conductive polymer.

In some embodiments the nanoparticle quantum dots 620 underneath the molecular imprints 604 are used to configure the imprints 604. In certain embodiments the quantum dots 620 or conductive cores 626 are custom-engineered to produce unique electron wave function configurations that modulate the response of the molecular imprints 604. The quantum dots 620, or cores 626 may be used to dynamically reconfigure the electron charge distribution within the molecular imprints 604, thereby creating a tunable molecular imprint 604 at the quantum level. Such charge distribution may influence process such as the capture, sensing, reporting, deactivation, or destruction of pathogens or other molecules.

For non-limiting example, static electric fields (also known as direct-current or DC fields) have been shown to repel, attract, or capture airborne molecules, particles, or gases. Such static electric fields are sometimes generated on the surface of the electronically enhanced molecular imprinted filtration element 500, with the use of interdigital electrodes 510 deposited onto or into the surface of an insulating material 508 (e.g. polyurethane foam), but lying beneath the polymer film 202 or molecular imprinted fabric 400, and corresponding molecular imprints 604.

In various embodiments electric fields, ultrasonic waves, light, or quantum dots 620 provide additional energy to free molecules from the imprint binding sites. This may function in the fabrication of the molecular imprints and in re-activation of the binding function of imprint sites that have been de-activated by the bonding of free molecules to the imprints.

In certain embodiments high frequency ultrasonic waves (10 MHz-10 GHz) or light (infrared to ultraviolet) may impact pathogens or other materials bound to the molecular imprints 604. The ultrasonic or light waves may be generated in the electronically enhanced molecular imprinted filtration element 500 or in an attachment and conducted to the filtration element 500 via waveguide principles, including without limitation an acoustic waveguide or optical fibers embedded into the electronically enhanced molecular imprinted filtration element 500. The electronically enhanced molecular imprinted filtration element 500 sometimes comprises a semiconductor. In certain embodiments the semiconductor comprises silicon into which ultrasonic transducers or lasers are fabricated on microchips and embedded into the filtration element 500 to locally excite the molecular imprints.

In certain embodiments high-frequency ultrasonic waves (10 MHz-10 GHz) are generated locally in the electronically enhanced molecular imprinted filtration element 500 by embedded piezoelectric elements 610 and conductive cores 608, 616, 622 and 626. In some embodiments an ultrasonic wave is generated on the electronically enhanced molecular imprinted filtration element 500 that mechanically agitates bound protein molecules or other materials and induces their separation from the imprints 204. Piezoelectric elements may include but are not limited to fibers and thin films.

Figure 7:
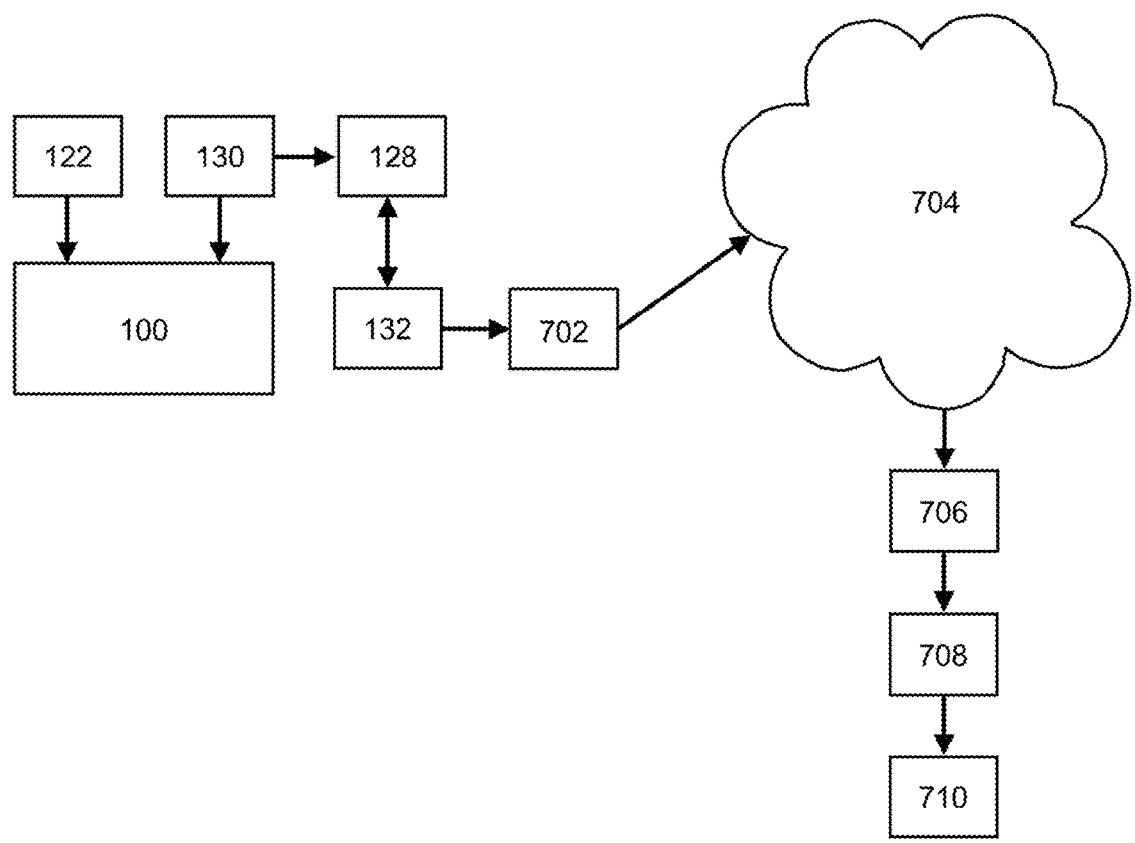
FIG. 7 is a schematic line drawing depicting an embodiment of a system for an electronically enhanced molecular imprinted air filter in accord with the present invention.

FIG. 7 depicts an embodiment of a system 700 for an electronically enhanced molecular imprinted air filter, the system 700 comprising an air filtration apparatus 100, a power supply 122, a sensor 130, a sensor controller 128, a reporting module 132, a communications module 702, a remote communication system 704, a receiving module 706, a repository 708 and a dispersing module 710.

In some embodiments the sensor controller 128 relays information from the sensor 130 to the reporting module 132. The reporting module 132 may provide a readable output or action command based on the level and/or type of hazardous substance or infectious pathogen detected by the sensor 130. In certain embodiments, the reporting module 132 generates a signal or alarm based on input from the sensor 130. The sensor module 128 and/or reporting module 132 sometimes generate an actionable command to the electronic enhancements triggering an action including without limitation re-tuning, loading, and/or emptying of the imprints. In various embodiments the communications module 702 receives input from the sensor controller 128 or the reporting module 132. The communications module 702 may send such input to the remote communication system 704 via, without limitation, an internet, a cloud, a telecommunication, or a database. Thus, an air system monitor local to the molecular imprinted air filter 100 or a remotely located monitor may be altered to read and/or communicate critical information related to the air quality.

In various embodiments a signal may trigger a dispersal of an air modifying substance or medication from the repository 708 via the dispersing module 710. In certain embodiments, a triggering signal from the sensor controller 128 is communicated to the power supply 122, where it triggers one or more of fine-tuning the molecular imprint 604 to enhance the response to a range of molecules, providing electrical energy to free molecules from the imprinted binding site, re-activating the specific molecule capture function of the imprint site, and interacting with the molecular imprint 604 to function as a biosensor.

In certain embodiments the sensor controller 128 comprises at least one of a photodetector to convert optical signals from optical fibers to electrical signals, an ultrasound transducer to convert acoustic signals from acoustic waveguides to electrical signals, a spectrometer to analyze optical signals with molecular spectroscopy (for example surface plasmon resonance, surface-enhanced Raman, stimulated Raman, Mie scattering, attenuated total reflectance, quantum dot fluorescence quenching, photoluminescence, and UV-VIS-IR spectroscopy), a multiplexer for a plurality of sensor channels, an amplifier to amplify sensor signals, a rectifier for radio-frequency signals such as ultrasonic signals, an electronic filter and/or discriminator to separate signals from noise, and a trigger signal generator.

EXAMPLES

Example 1: The Manufacture of a Molecular Imprinted Air Filter

A procedure for creating molecular imprints on an air filtration element comprises the following steps. (1) Molecules of a specific airborne molecule (for example, COVID-19 virus) or a specific protein that functions as an antigen, antibody, or binding site for the airborne molecule are absorbed onto the surface of a thin mica sheet. (2) A buffer is added to neutralize the pH of the mica-protein surface. (3) The mica sheet-buffer solution is heated and subsequently cooled. (4) The mica sheet is rinsed with deionized water and spin cast with a disaccharide to allow coating.

The hydroxyl groups on the disaccharide molecules, combined with the surface polar residues of the protein molecules, facilitate the formation of hydrogen bonds during dehydration. Hydrogen bonds are vital for molecular recognition in biological signaling. The disaccharide coating also protects the protein molecules from dehydration and damage during the following plasma deposition process, thus preserving the fidelity of the imprinted cavities.

(5) A thin fluoropolymer film is deposited onto the mica surface using radio-frequency glow-discharge plasma deposition and hexafluoropropylene. (6) The fluoropolymer film is removably attached to a temporary support surface. The surface provides mechanical support for the fluoropolymer film. (7) The mica sheet is peeled from the supported fluoropolymer film. (8) The protein molecules are removed from the fluoropolymer film using a solvent wash, leaving behind molecular imprints of the protein. (9) The fluoropolymer film is incorporated into a woven or non-woven air-permeable surface.

For the synthesis of molecular imprinted fibers, silica capillaries are used as molds to replace the mica sheet. As in the procedure above, the target molecules are absorbed onto the interior surface of the capillary. The support polymer is then introduced into the capillary and polymerized. The capillaries are then etched away to free the imprinted polymer fibers. Another approach for the synthesis of molecular imprinted fibers is to use silica fibers as a permanent substrate for the molecularly imprinted polymer. The silica fibers are coated with a thin layer of the molecularly imprinted polymer and the polymer is then polymerized.

The above procedures may be utilized to molecularly imprint a set of diverse proteins onto an air filter in a specific spatial pattern. Non-limiting examples of proteins and other macromolecules that could be used for each molecular-imprinted polymer region on the air filter include the following: (1) angiotensin-converting enzyme 2 (ACE-2), which functions as the entry point into cells for the COVID-19 virus and other coronaviruses; (2) complex sugar chains (glycans) such as sialic acids of various chemical forms, which function as the entry point into cells for influenza viruses; and (3) receptor molecules in the immunoglobulin superfamily (IgSF), which function as entry points into cells for the measles virus and rhinovirus (common cold).

In the event that certain molecular imprints do not function similarly to their protein molecule counterparts, molecular "outprints" can be created by a stamping method that first creates the molecular imprints on nanoparticles. A polymer film is then stamped with these molecularly imprinted nanoparticles, creating a negative image of the molecular imprint, or an outprint. These molecular outprints will have the same positive shape as the original molecule, and may, therefore, have a functionality more similar to the original molecule.

Example 2: Detection of Virus Proteins

Protein-based molecular imprints have additionally been explored for the detection of virus proteins and even whole viruses. In some cases, a polymer is cross-linked and co-polymerized in the presence of a target molecule or protein. This target acts as a template for creating a cast. Once the cast is removed, it creates space for an active binding site. Molecular imprinting is supported by extensive research in the last decade, yet the application of imprinting protein-binding sites on dry surfaces for capture, sensing, activation and deactivation of airborne molecules remains to be investigated.

Previous studies have demonstrated the binding of influenza viruses to molecular imprints using aqueous solutions of viruses in contact with an imprinted polymer. In the event that an aqueous environment may be necessary for the binding of viruses to molecular imprints, evidence supports a mechanism for the capture, sensing, activation and deactivation of airborne viruses by a molecular imprinted air filter. This evidence includes the fact that many pathogenic viruses such as influenza and COVID-19 are primarily spread by microscopic airborne droplets (microdroplets) that are dispersed from an infected person by coughing, sneezing, singing, and/or speaking. Upon passing through a molecular imprinted air filter, the microdroplets or aerosolized pathogens are trapped by fibers and/or pores, and simultaneously come into contact with molecular imprints on the fiber and/or pore surfaces. Interaction of molecular imprints with pathogens may be further enhanced by a thin film of water coating the molecular imprints. Consequently, the viruses are brought into contact with the molecular imprints in an aqueous environment.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

I claim:

1. A molecular imprinted air filter apparatus for removing, detecting and/or reporting specific agents and/or molecules, the apparatus comprising:
   a. A molecular imprinted air filter comprising an air filtering component comprising one or more air-permeable layers of molecular imprinted fabric, woven material, non-woven material and/or a porous material positioned to contact molecules and/or agents in an airborne, and/or microdroplet-borne environment;
   b. a bioactive molecular imprint wherein an imprinted or outprinted cavity is of at least one of a bioactive molecule that captures a specific airborne, fluid borne, and/or microdroplet-borne molecule, particle, or agent, and of a protein with a binding site that captures a specific airborne, fluid borne, and/or microdroplet-borne molecule, particle, or agent;
   c. a power supply and
   d. an electronic enhancement integrated and dispersed or deposited into or onto at least one of the material volume and the surface of the air filtering component of the air filter apparatus, wherein the electronic enhancement comprises at least one of an electrode, a semiconductor, a nanoparticle quantum dot, a nano-island, a quantum wire, other nanostructured component, a piezoelectric element, an acoustic waveguide, an optical waveguide, a transducer, a sensor wire, a biomimetic microchip, and a laser.

2. The apparatus of claim 1 wherein the molecular imprinted air filtering component comprises an air-permeable material comprising at least one of paper, polymer foam, woven fabric, knitted fabric, non-woven fabric, meltblown fabric, ion-infused fabric, a non-fabric material and a hydrophilic material to capture microscopic airborne droplets to enable the interaction of a plurality of the molecular imprinted cavity with airborne hazardous substances and/or infectious pathogens in an aqueous environment.

3. The apparatus of claim 2 further comprising an air intake avenue and an air output avenue.

4. The apparatus of claim 3 further comprising a fluid supply and associated fluid atomizer.

5. The apparatus of claim 1, wherein the electrode functions as an interdigital electrode for at least one of enhancing, modulating, and reading the binding state of the imprinted cavities.

6. The apparatus of claim 5 wherein the interdigital electrode comprises at least one of comb-shaped interlocking arrays of straight parallel electrodes, a fan-shaped array of radially-oriented electrodes, an array of concentrically-oriented circular electrodes, and arrays consisting of electrodes arranged in more complex geometries such as elliptical, parabolic, hyperbolic, and straight-line angles.

7. The apparatus of claim 6, wherein the electronic enhancement at least one of generates a static and time-varying electrical field, produces an electron wave function configuration that dynamically reconfigures the electron charge distribution within the molecular imprint, enables fine tuning of the imprinted cavity to enhance its response to a range of molecules, generates at least one of ultrasonic and electromagnetic waves providing energy to free molecules from the imprinted cavity, mechanically agitates a biomolecule to induce its interaction with or release from the imprinted cavity and re-activates the specific molecule capture function of the imprinted cavity.

8. The apparatus of claim 1 wherein at least one of the molecular imprinted filter and the imprinted cavity comprises a biosensor for at least one of a specific health condition, a specific type of pathogen, a specific type of pollutant, a specific type of allergen, and a specific environment or condition and/or is customized to a specific user or set of users.

9. The apparatus of claim 8 wherein the biosensor comprises a molecular imprinted polymer surface comprising at least one of surface plasmon resonance (SPR), surface-enhanced Raman spectroscopy (SERS), stimulated Raman spectroscopy (SRS), Mie scattering spectroscopy, fluorescence quenching of semiconductor quantum dots, photoluminescence, UV-visible spectroscopy, attenuated total reflection (ATR) spectroscopy, electrochemical sensors (conductivity, capacitance, impedance, potentiometry, and voltammetry measurements), piezoelectric sensors (quartz crystal microbalance, acoustic waveguide, surface acoustic wave (SAW), pulse-echo ultrasound, through-transmission ultrasound, and phased-array ultrasound), and biomimetic microchips with micropatterned imprinted polymers.

10. The apparatus of claim 9 wherein the electronic enhancement at least one of reads the binding state of the molecular imprinted cavities to detect hazardous airborne and/or microdroplet-borne agents, reports the presence of a specific agent, and triggers re-tuning the imprinted cavities in response to at least one of a completed reaction and a changing molecular environment.

11. The apparatus of claim 1, comprising one or a plurality of types of the molecular imprinted cavity and wherein the one or more air-permeable layers of molecular imprinted fabric of the filtering component catalyze a biochemical reaction with an airborne, fluid borne, and/or microdroplet-borne agent to attenuate, neutralize, and/or detect the agent.

12. The apparatus of claim 1, wherein each of the one or more air permeable layers of molecular imprinted fabric of the filtering component catalyzes a particular step of the biochemical reaction with an airborne and/or microdroplet-borne agent to attenuate, neutralize, and/or detect the agent.

13. The apparatus of claim 12, wherein layer (n) of the one or more air permeable layers of molecular imprinted fabric catalyzes a distinct biochemical reaction (p) in a multistep reaction with an airborne and/or microdroplet-borne agent.

14. He apparatus of claim 13 wherein layer (n+1) of the one or more air permeable layers of molecular imprinted fabric catalyzes a successive biochemical reaction (p+1) in a multistep reaction with an airborne and/or microdroplet-borne agent.

15. The apparatus of claim 14, wherein a plurality of imprinted cavity types catalyzes a multistep biochemical reaction to attenuate, neutralize, or detect an airborne and/or microdroplet-borne agent.

16. The apparatus of claim 15, wherein the plurality of imprinted cavity types simultaneously catalyze a one or more biochemical reaction to at least one of attenuate, neutralize, detect, and report one or more hazardous airborne and/or microdroplet-borne agents.

\* \* \* \* \*